(12) United States Patent
Stark

(10) Patent No.: US 7,397,566 B2
(45) Date of Patent: *Jul. 8, 2008

(54) METHOD AND APPARATUS FOR OPTICAL INTERACTANCE AND TRANSMITTANCE MEASUREMENTS

(76) Inventor: Edward W. Stark, 160 W. End Ave., Suite 3M, New York, NY (US) 10023

( * ) Notice: Subject to any disclaimer, the term of this patent is extended or adjusted under 35 U.S.C. 154(b) by 0 days.

This patent is subject to a terminal disclaimer.

(21) Appl. No.: 11/508,774

(22) Filed: Aug. 23, 2006

(65) Prior Publication Data

US 2007/0052967 A1    Mar. 8, 2007

Related U.S. Application Data

(63) Continuation of application No. 08/818,289, filed on Mar. 14, 1997, now Pat. No. 7,142,307, which is a continuation of application No. 08/385,073, filed on Feb. 7, 1995, now abandoned, which is a continuation of application No. 08/062,738, filed on May 14, 1993, now abandoned, which is a continuation of application No. 07/663,144, filed on Mar. 1, 1991, now abandoned.

(51) Int. Cl.
   *G01N 21/47* (2006.01)
(52) U.S. Cl. ............... 356/446; 356/442; 356/239.1
(58) Field of Classification Search ............ 356/41, 356/434, 442, 445, 446, 239.1; 385/12, 115; 250/227.28
   See application file for complete search history.

(56) References Cited

U.S. PATENT DOCUMENTS

| | | | |
|---|---|---|---|
| 3,310,680 A | 3/1967 | Hasegawa | 356/341 |
| 3,733,137 A | 5/1973 | Badessa | 356/434 |
| 3,786,266 A | 1/1974 | Reid et al. | 250/222.1 |
| 3,994,602 A | 11/1976 | Howarth | 356/442 |
| 4,054,391 A | 10/1977 | Witte | 356/445 |
| 4,082,458 A | 4/1978 | Fukui et al. | 356/73 |
| 4,188,121 A | 2/1980 | Hirleman, Jr. et al. | 356/336 |
| 4,213,462 A * | 7/1980 | Sato | 600/477 |
| 4,226,541 A | 10/1980 | Tisue | 356/446 |
| 4,573,761 A * | 3/1986 | McLachlan et al. | 385/115 |
| 4,583,858 A | 4/1986 | Lebling et al. | 356/402 |

(Continued)

FOREIGN PATENT DOCUMENTS

EP    32774    7/1981

(Continued)

*Primary Examiner*—Layla G. Lauchman
*Assistant Examiner*—Juan D Valentin
(74) *Attorney, Agent, or Firm*—Beck & Tysver P.L.L.C.

(57) ABSTRACT

A method, system and apparatus for improving at least one of a) optical interactance measurements, b) optical transmittance measurements and c) optical reflectance measurements. The apparatus has a probe having a body portion and an tip portion. The body portion has a central tubular element having an opening therethrough. The tip portion has a central aperture and a number that is a plurality of ring openings therein. At least some of the plurality of rings are angled with respect to a longitudinal axis of the probe. A plurality of fiber optic bundles corresponds in number at least to the number of ring openings, and at least one fiber optic bundle is arranged at one end of the longitudinal axis for receiving specimen information and at another end of the longitudinal axis connected to a detector for receiving a signal.

3 Claims, 2 Drawing Sheets

U.S. PATENT DOCUMENTS

| | | | | |
|---|---|---|---|---|
| 4,627,014 | A | 12/1986 | Lo et al. | 702/25 |
| 4,633,087 | A | 12/1986 | Rosenthal et al. | 250/339.12 |
| 4,711,580 | A | 12/1987 | Venable | 356/406 |
| 4,800,885 | A | 1/1989 | Johnson | 600/330 |
| 4,884,891 | A | 12/1989 | Borsboom | 356/446 |
| 4,989,985 | A | 2/1991 | Hubble, III et al. | 356/445 |
| 5,003,500 | A | 3/1991 | Gerber | 356/319 |
| 5,057,695 | A | 10/1991 | Hirao et al. | 250/575 |
| 7,142,307 | B1 * | 11/2006 | Stark | 356/446 |

FOREIGN PATENT DOCUMENTS

| | | |
|---|---|---|
| EP | 0 351 994 | 1/1990 |
| JP | 2 14842 | 12/1983 |
| JP | 163545 | 9/1984 |
| JP | 57236 | 4/1985 |
| WO | WO 91/17697 | 11/1991 |

* cited by examiner

METHOD AND APPARATUS FOR OPTICAL INTERACTANCE AND TRANSMITTANCE MEASUREMENTS

RELATED APPLICATIONS

This application is a continuation of U.S. patent application Ser. No. 08/818,289 filed Mar. 14, 1997 now U.S. Pat. No. 7,142,307, which is a continuation of Ser. No. 08/385,073 filed Feb. 7, 1995 now abandoned, which is a continuation of Ser. No. 08/062,738 filed May 14, 1993 now abandoned, which is a continuation of Ser. No. 07/663,144 filed Mar. 1, 1991 now abandoned.

FIELD OF THE PRESENT INVENTION

The present invention relates to an improved method and apparatus for performing optical interactance and transmittance measurements and, in particular, such method and apparatus where undesired information is discriminated against and desired information is enhanced. Reflectance measurements on small amounts of specimen are also encompassed by the invention.

BACKGROUND OF THE PROBLEM SOLVED BY THE PRESENT INVENTION

When optical energy is transmitted through a diffuse medium, scattering causes redirection of the rays so that the geometric pathlength between the energy entrance point and the energy exit point no longer defines the distance energy travels within the specimen. In addition, substantial energy may be scattered back towards the entrance or otherwise away from the exit region where detection occurs, thereby reducing the detected signal. This signal is therefore variable depending on the scattering characteristics of the particular region of the specimen traversed by the optical radiation.

A further cause of interference is nonhomogeneous or layered distribution of specimen characteristics, e.g., the layers of skin and fat which cover muscle tissue, the skin which covers the flesh of a fruit or vegetable, or the coating of windows through which measurements are to be made. Often, it is desirable to eliminate the effects of the surface layers to provide information on the underlying portions of the specimen. The present invention is directed to solving these problems which cause inaccuracies in spectroscopic determination of qualitative or quantitative characteristics of the specimen.

An additional problem is the making of diffuse reflectance and transmittance measurements on small specimens. Present reflectance instruments are generally designed to illuminate the specimen and detect reflected energy over several square centimeters of area. It is sometimes necessary to work with small amounts of specimen, for example a single seed, which must be recovered intact for future use. The present invention also addresses both diffuse transmission and diffuse reflection measurements of small specimens.

BACKGROUND PRIOR ART

There has been a proposal for use of a transmission cell which had two different pathlengths through the specimen as a means of extending the dynamic range of spectral measurements in clear solutions. This proposal did not encompass separate measurement of the signals for the two pathlengths but rather the combined optical energy was detected. This results in a very nonlinear signal relative to concentration of an analyte within the specimen, however, the nonlinearity is predictable based on the known optical geometry of the cell.

Dual pathlength transmission cells with separate detection have been proposed to remove the effects of window coating in transmission measurements through clear liquids. This approach is equivalent to placing a second cell of different thickness in the reference beam of a dual-beam spectrometer. Effects common to the two paths, such as absorption due to the window material, equal deposits on the windows, atmospheric absorption, and the specimen absorption in the equal portion of the pathlength are canceled by taking the simple ratio of the signals derived from the two paths.

Norris ["A New Approach for the Estimation of Body Composition: Infrared Interactance", Joan M. Conway, Karl H. Norris and C. E. Bodwell, American Journal of Clinical Nutrition, Vol. 40, pp. 1123-1130 (1984)] first proposed measurement by means of "interaction", whereby a diffuse specimen is illuminated at one location and energy is collected some distance away on the same surface of the specimen. This is similar to diffuse reflection in that the primary mechanism returning energy to the detector is scattering, i.e., in the absence of scattering within the specimen, the incident energy would not impinge on the detection region. It differs from diffuse reflection, however, because the detection region does not include the illumination region, but is separated from it by some distance. Therefore, surface reflection of energy does not contribute to the detected signal and all the detected energy has traversed a minimum distance within the specimen, the separation distance between the source and detector. In this sense, "interaction" is similar to diffuse transmission. In general, the effective depth of penetration and the effective pathlength both increase as the spacing between the source and detection locations is increased.

Norris and others applying his method have used a single measurement of the energy passing through the specimen from the source region to the detection region. Typically, uniform geometric spacing between the source area and the detection area is provided by using a central aperture surrounded a small distance away by a ring aperture. Either aperture could serve for the source while the other is used for detection. Both apertures are usually in contact with the specimen to prevent energy from leaking between the source and detection regions without traversing the specimen although thin windows between the apertures and the source have been used. An alternative structure has been to use equally parallel slit apertures, alternating between source and detection functions. In this case, all the source slit apertures were illuminated through one fiber optic bundle while energy was collected from all the detection apertures by means of a second bundle. Therefore, although more than two apertures exist, there is only one detected signal.

Diffuse transmittance and reflectance measurements are usually made on large volumes of specimen to reduce errors by averaging the inhomogeneities. When only small specimens are available, the usual procedure is to grind each specimen into a fine powder and mix it with a nonabsorbing diluent or to spread it on a diffusely reflecting background so as to present a large area for reflectance measurement. There has been a proposed use of a reflecting cone into which the specimen is placed. The incident energy which does not impinge the specimen is returned in the direction of the source, and is rejected by the diffuse reflectance detection geometry. Norris ["Determination of Moisture in Corn Kernels by Near-Infrared Transmittance Measurement", E. E. Finney, Jr. and Karl H. Norris, Transactions American Society of Agricultural Engineers, Vol. 21, pp. 581-584 (1978)] has made diffuse transmission measurements on single seeds by focusing the energy on the seed and placing a large area detector behind the opposite side. Careful attention must be paid to block the direct path past the seed. These methods for handling intact small samples have been inconvenient at best.

SUMMARY OF THE INVENTION

In accordance with the invention, a method for improving optical interactance measurements comprises the steps of providing illumination by way of a plurality of paths through a specimen having a characteristic to be measured, sensing two or more independent signals developed at the same time or in rapid sequence representing optical information from said specimen and processing said signals in accordance with appropriate modeling techniques to minimize inaccuracies in spectroscopic determination of qualitative of quantitative characteristics of the specimen.

Also in accordance with the invention, apparatus for improving optical interactance measurements comprises means for providing illumination through a specimen having a characteristic to be measured along a plurality of different paths, means for sensing optical information provided from an illuminated specimen, means for developing a plurality of independent signals corresponding in number to said plurality of paths, the signals representing the optical information obtained from the specimen and means for processing the signals in accordance with appropriate modeling techniques to minimize inaccuracies in spectroscopic determination of quantitative or qualitative characteristics of the specimen.

For a better understanding of the present invention, reference is made to the following description and accompanying drawings while the scope of the invention will be pointed out in the appended claims.

DESCRIPTION OF THE INVENTION AND PREFERRED EMBODIMENTS

A first aspect of this invention comprises the use of three or more optical apertures shared among the source and illumination functions so as to provide two or more independent signals for further processing and analysis. For example, in FIG. 1, a probe utilizing fiber optics is shown which has two ring apertures surrounding a central round aperture.

Figure 1:
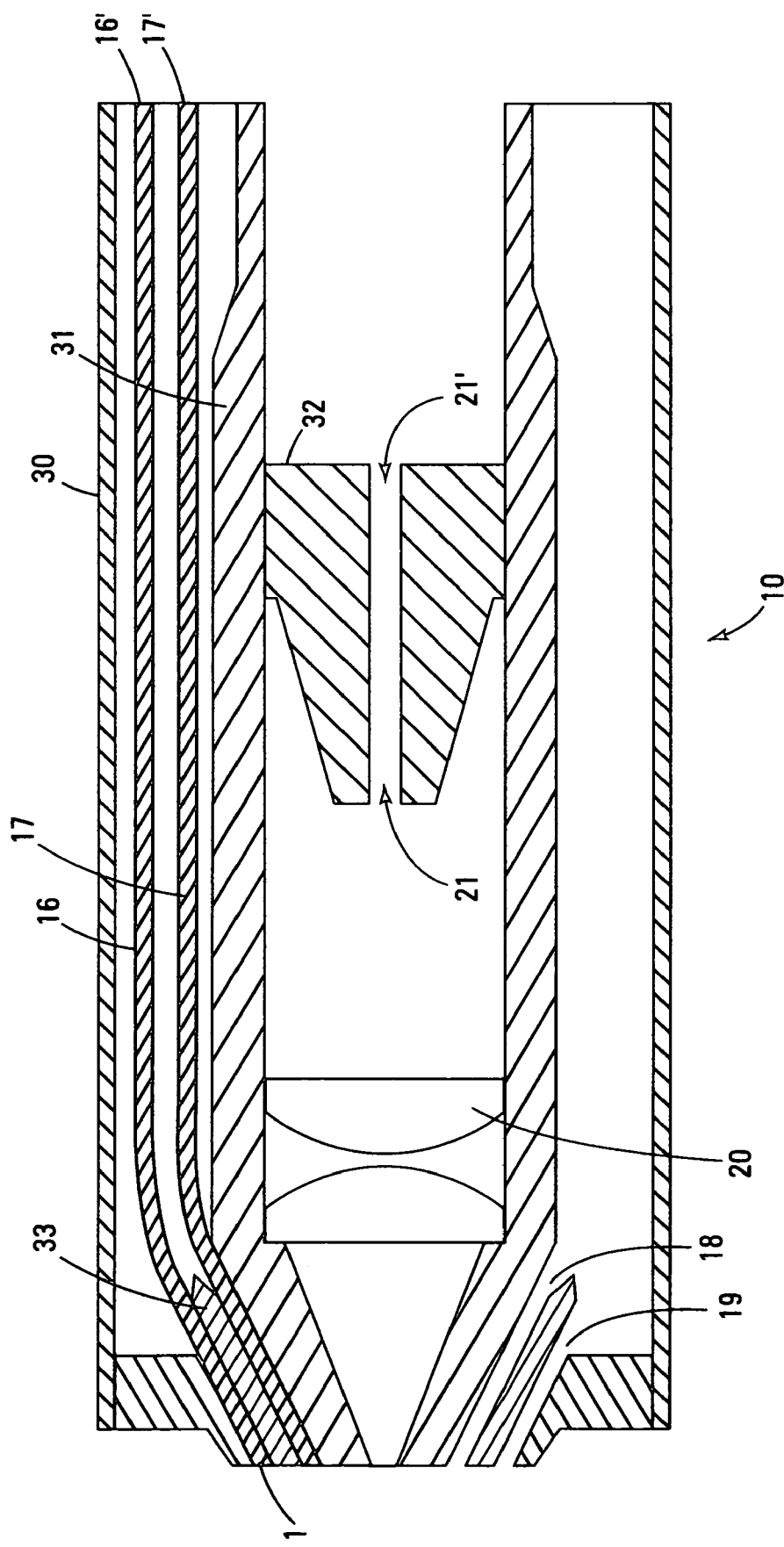
FIG. 1 is a cross-sectional, length-wise view in partially schematic form of a two-ring, central aperture probe in accordance with the invention.

In FIG. 1, the probe 10 includes a cylindrical outer body 30 in which a concentric inner body 31 is arranged. The inner body 31 tapers at the examining end to a central aperture 15. The outer body 30 constricts at the examining end to define a conical, inwardly directed wall. The tapered end of the inner body 31 defines a second conical wall. Between these two walls 30, 31 is disposed a conical dividing element 33. The angles defined by the two walls and the conical dividing element are preferably the same. Conical annular spaces or rings (shown in cross-section as 14, 13, 12 and 11) are defined by the two walls and dividing element. In these annular spaces or rings are disposed, in conical fashion, optical fibers 16 and 17 for supplying illumination to the specimen. Within the inner body 31 are disposed one or more lenses 20 for focusing and transmitting incident light entering the aperture 15. A central fiber element 21, supported by element 32, receives light from the lenses 20, and directs it to the exit portion 21' of the probe. Illumination for fibers 16 and 17 is provided at 16' and 17'.

In this apparatus, each ring is used for illumination by fiber optic elements while the central detection aperture is connected by fiber optics to a detection system, such as a diode-array spectrophotometer. The central aperture in one embodiment is 1.2 mm diameter, and the inner ring has a mean diameter of 6 mm with a width of 1 mm. The mean spacing from the inner ring to the central aperture is therefore 3 mm and the minimum spacing is 1.9 mm. The outer ring has a mean diameter of 12 mm and a width of 1 mm, providing a mean spacing from source to detection of 6 mm and a minimum spacing of 4.9 mm.

In a preferred arrangement, the tip portion of the probe and the fiber optic elements at the tip portion are angled at approximately 26° with respect to the longitudinal axis of the probe.

It will be noted in FIG. 1 that the central detection assembly is movable axially. For interactance measurements, the detection aperture at the distal end of this assembly is normally positioned in the same plane as the source ring apertures, however, it may be moved back and lenses inserted so as to image a detection area on the specimen into the aperture of the detection fibers. The lenses 20 in the inner body of the probe are interchangeable and the positions of the lenses and the central detection assembly are adjustable by means of spacers. In one embodiment, lenses and arrangements for three different specimen sizes for reflectance and one arrangement for interactance are listed in the following Table 1:

TABLE 1

| Stack Position | REFLECTANCE | REFLECTANCE Specimen Size | REFLECTANCE | |
|---|---|---|---|---|
| | 1.2 mm | 0.7 mm | 2.0 mm | INTERACTANCE |
| 1 | 21 mm f length Plano-Convex Melles Griot 01LPX023 | 21 mm f length Plano-Convex Melles Griot 01LPX023 | 15.9 mm spacer | Fiber Optic Holder for central fiber |
| 2 | 6 mm spacer | 6 mm spacer | Melles Griot 01LPX065 | Spacer |
| 3 | 21 mm Melles Griot 01LPX023 | 36 mm Melles Griot 01LPX065 | 6 mm spacer | Spacer |
| 4 | 17.7 mm spacer | 17.7 mm spacer | 21 mm Melles Griot 01LPX023 | Spacer |

TABLE 1-continued

| Stack Position | REFLECTANCE 1.2 mm | REFLECTANCE Specimen Size 0.7 mm | REFLECTANCE 2.0 mm | INTERACTANCE |
|---|---|---|---|---|
| 5 | 15 mm spacer | 15.9 mm spacer | 17.7 mm spacer | Spacer |
| 6 | Fiber Optic Holder for Central Fiber | 15 mm spacer | 15 mm spacer | Spacer |
| 7 | 15.9 mm spacer | Fiber Optic Holder for Central Fiber | Fiber Optic Holder for Central Fiber | Spacer |

This reimaging allows control of the size of the detection area and the angular cone within which energy is detected by changing the lenses and their spacing.

It may also be seen in FIG. 1 that the energy source fibers are arranged in conical form. The energy exits at a mean angle of approximately 45° based on the angle of the fibers and the refraction at their polished ends. For interactance measurements on specimens which have limited backscatter, introduction of the energy at an angle directed toward the detector improves the efficiency. This feature also provides for diffuse reflectance and transmittance measurements using the same probe as discussed below.

Figure 2:
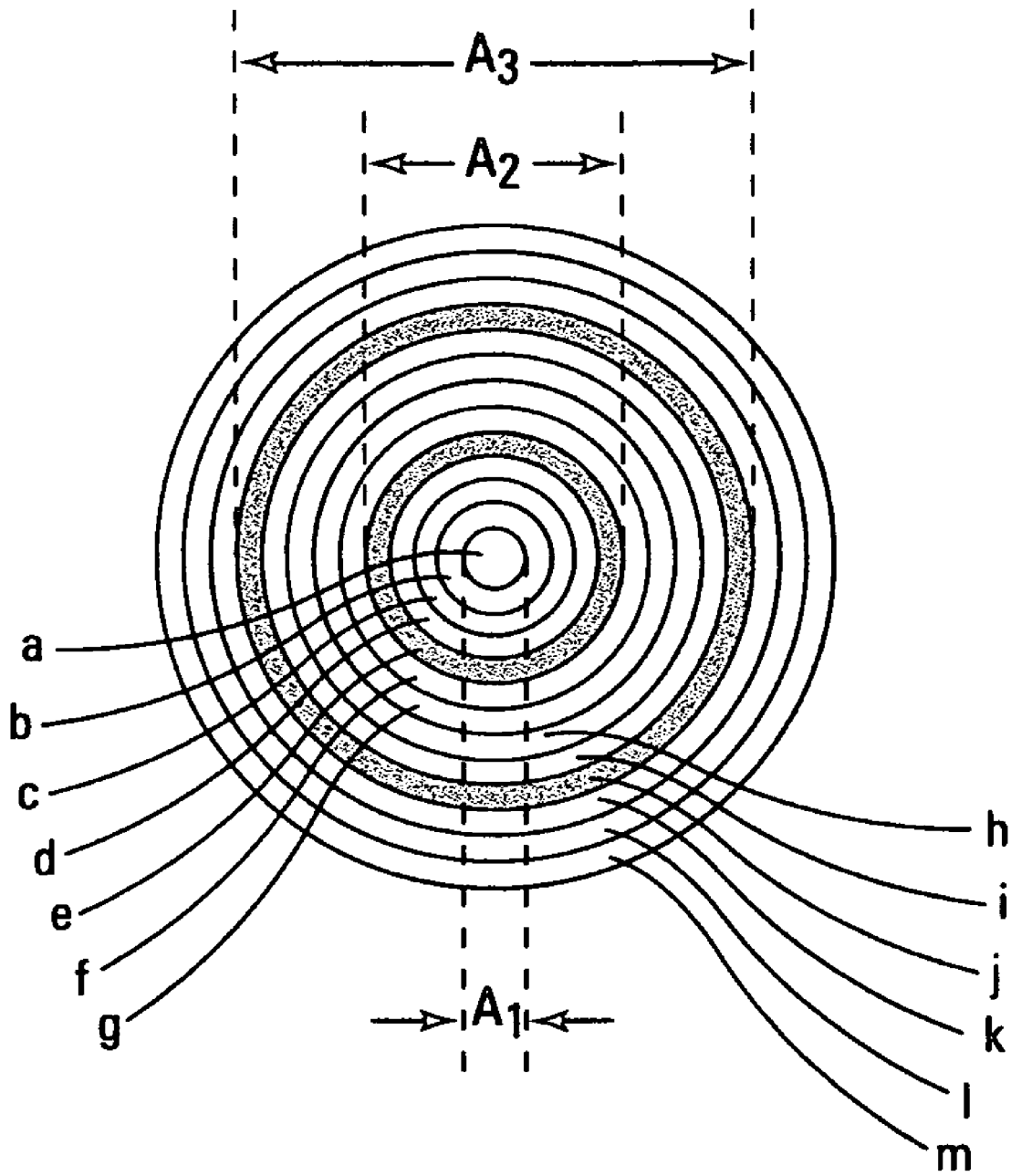
FIG. 2 is a diametric cross-section of a probe exhibiting a multiple ring aperture structure in accordance with the invention.

In order to obtain separate signals for each spacing, the two source rings may be alternately illuminated or the source energy may be modulated differently, e.g., at two different frequencies or with different time sequence codes. The detection signal is then gated or demodulated to separate the information from the two different sources. Each source fiber optic bundle, preferably, has a small percentage of its input fibers brought out so that the associated source intensity and modulation can be monitored. It will be obvious to one skilled in the art that additional source rings may be provided, each with its distinctive modulation, and that the operation may be reversed to provide a single source by using two or more detection rings coupled to multiple or time-shared detection means. For example, FIG. 2 shows a design comprising 10 large area (8 to 28 mm$^2$ active area) ring apertures, nominally designated as source rings, and a central aperture plus 2 additional rings of smaller area (2.9 to 3.4 mm$^2$) nominally considered as detection rings. The source ring active area is adjusted by the density of active fibers within each ring. This structure allows selection of a wide variety of spacings and locations for the measurements using combinations of the three different detection apertures and 10 source apertures. While the examples shown here show ring geometries, other geometries, such as parallel slits or small apertures, which provide substantially constant values of the spacing between all points within a given source aperture and those within a given detection aperture may be used.

Having derived separate signals for the two or more paths, they are processed and combined in accordance with a linear or nonlinear model of the system response to variations in the concentration of the analytes and interferences present in the spectrum. In the simplest cases, for example, the cancellation of the optical effects of deposits on the window through which the measurements are being made, it may suffice to use the ratio of the signal from one spacing to that of a second spacing. This assumes that the deposits have the same transmission spectrum $T_1$ for both paths, as would be true for a uniform coating, and that the specimen behind the window is relatively homogeneous with an interactance spectrum, I. The signals may then be expressed as $K_1*T_1*I_1$ and $K_2*T_1*I_2$ where $K_1$ and $K_2$ are system functions involving the relative source intensities, the gain through the system, scattering losses and similar factors. The ratio is therefore $(K_1/K_2)*(I_1/I_2)$ and the window coating transmission has been eliminated from the result. Note that any factors common to $K_1$ and $K_2$ are also canceled as in the normal use of a reference and the remainder factors may be adjusted so that the K factor becomes unity. Taking the log of the ratio yields "absorbance" A equal to $\log(I_1)-\log(I_2)$. If I is exponentially related to the product spacing t and the analyte absorptivity a, log(I) will equal (a*t) and the log difference becomes $a*(t_1-t_2)$ where a is the "absorptivity" spectrum which is linearly related to concentration. In many, if not most, practical cases, log (I) is not linearly related to the product of spacing with absorptivity and absorptivity is not linearly related to concentration. Therefore, this invention contemplates use of other linear and nonlinear chemometric models to define the relationships and provide quantitive analyte information.

The situation is further complicated if the specimen is nonhomogeneous, such as the cases with layers described above. Here, the various signals are derived by absorption of light through different combinations of materials within the specimen. All the signals contain information on the surface layers while the signals derived from the larger spacings contain information on the deeper layers that is diminished or lacking in the signals measured with smaller spacings. When it is desired to differentiate between the information derived from deep within the sample and that obtained from layers closer to the surface, these signals may be combined in a linear or nonlinear chemometric model so as to extract the desired information. In this case, it is helpful to have the input energy for each source aperture as an additional measured quantity for use in the modeling. Each class of specimens requires a different form of model, and subclasses require determination of various model parameters during the calibration process.

Another aspect of the invention is the use of the probe for diffuse reflection measurements of small specimens. The specimen may be held in a small hole drilled in a flat plate mounted approximately 2 to 4 mm from the end of the fiber-optic probe. It is illuminated via one or both of the outer ring bundles at an angle of incidence of approximately 45 degrees. The plate is finished with a mirror surface so that incident energy outside the area of the specimen is reflected at approximately 45 degrees from the normal. The diffusely reflected energy is collected by imaging the specimen surface on the central fiber bundle via lenses whose optical axes are coincident with the axis of the probe assembly. The power and spacing of the lenses may be selected so as to select the desired sample area. Because the collection is normal to the specimen and specimen holder and energy is reflected by the holder and by any window above the specimen at an angle, this specularly reflected energy is rejected from the measurement. If desired, a diffuse or specular reflector may be placed behind the specimen to increase its apparent depth by a factor of at least two.

Alternatively, the axis of the probe may be positioned vertically with the apertures at the top and a transparent window, such as a microscope slide, positioned with its upper surface at the appropriate distance from the apertures. Specimens may be placed on the window for measurement. Three measurements may be made:

a) no specimen (just a slide);
b) specimen
c) reference spectrum using a diffuse reflecting material such as SPECTRALON™ (a trademark of Labsphere, Inc.).

The "no specimen" energy spectrum is subtracted from the spectrum of the specimen and the spectrum of the reference to correct for residual energy reflected or scattered from the window.

Still another aspect of the invention is the measurement of diffuse transmission through small specimens. The specimen is mounted in a hole on a plate and illuminated as previously described for reflectance measurements. The receiving fiber-optic bundle is placed behind the sample so as to collect the transmitted energy. The conical illumination pattern is helpful in achieving rapid diffusion of energy within the specimen thereby improving the repeatability of measurements on small specimens. In addition, by using two collecting fiber-optic bundles, simultaneous or time shared measurement of both, the diffusely transmitted and diffusely reflected energy is possible. The combination of these two measurements allows additional information to be obtained concerning the absorption and scattering characteristics of the specimen.

Still another embodiment utilizes the probe as described above for reflection and an additional fiber bundle is employed behind the specimen to illuminate it. Therefore, the same receiver is utilized for transmittance and reflectance with two different illumination sources being provided. A switching arrangement may be used to alternate between the illumination sources.

In each case, the central detection element may comprise the detector itself rather than the fiberoptic detector bundle.

In FIG. 2, thirteen concentric circular regions (A1, A2, A3, a, b, C, d, e, f, g, h, i, and j) are shown. Regions A1, A2, and A3 are detection apertures and regions a through j are source apertures. The dimensions and properties of these regions are shown in Tables 2 and 3.

TABLE 2

Detection Aperture Dimensions

| Detection Aperture | Outside Diameter mm | Inside Diameter mm | Area mm² |
|---|---|---|---|
| A1 | 1.92 | 0.00 | 2.90 |
| A2 | 7.81 | 7.55 | 3.20 |
| A3 | 15.31 | 15.17 | 3.37 |

TABLE 3

Source Aperture Configurations

| Region | Inside Diameter_mm | Outside Diameter_mm | Area mm² | Active Area % | Active Area mm² | Ref. Fiber % | Ref. Fiber mm² |
|---|---|---|---|---|---|---|---|
| a | 1.92 | 3.85 | 8.8 | 90 | 7.90 | 10 | 0.9 |
| b | 3.85 | 5.70 | 14.5 | 90 | 13 | 10 | 1.45 |
| c | 5.70 | 7.55 | 20.2 | 90 | 17.2 | 10 | 2.0 |
| d | 7.81 | 10.21 | 34 | 50 | 17 | 5 | 1.7 |
| e | 10.21 | 12.66 | 43 | 50 | 21.5 | 5 | 2.2 |
| f | 12.66 | 15.17 | 52 | 50 | 26 | 5 | 2.6 |
| g | 15.31 | 17.30 | 51.1 | 40 | 20.4 | 4 | 2 |
| h | 17.30 | 19.30 | 57.5 | 40 | 23 | 4 | 2.3 |
| i | 19.30 | 21.30 | 63.7 | 40 | 25.5 | 4 | 2.6 |
| j | 21.30 | 23.30 | 70 | 40 | 28 | 4 | 2.8 |

For improving one of optical interactance measurements, optical transmittance measurements or optical reflectance measurements, the system incorporates a processor receiving signals from the apparatus comprising signal information, and software in the processor performs an analytic procedure on the information to provide information regarding the specimen.

While the above described probe is preferred, an alternate embodiment can be constructed where the direction of light flow can use the light source being provided at the control aperture and one or more of the fiber optic bundles responsive to specimen information.

While the foregoing description and drawings represent the preferred embodiments of the present invention, it will be obvious to those skilled in the art that various changes and modifications may be made therein without departing from the true spirit and scope of the present invention.

What is claimed is:

1. Apparatus for improving at least one of a) optical interactance measurements, b) optical transmittance measurements and c) optical reflectance measurements comprising:
    a probe having a body portion and an tip portion;
    the body portion comprising a central tubular element having an opening therethrough;
    the tip portion having a central aperture and a number that is a plurality of ring openings therein;
    at least some of the plurality of rings being angled with respect to a longitudinal axis of the probe;
    a plurality of fiber optic bundles corresponding in number at least to the number of ring openings, and at least one fiber optic bundle arranged at one end of the longitudinal axis for receiving specimen information and at another end of the longitudinal axis connected to a detector for receiving a signal.

2. A method for receiving specimen information and analyzing specimen information comprising placing said one end of the apparatus of claim 1 against a surface providing specimen information, detecting transmitted specimen information at the another end, and analyzing detected specimen information.

3. A system for for improving at least one of a) optical interactance measurements, b) optical transmittance measurements and c) optical reflectance measurements comprising:

the apparatus of claim 1;
a processor receiving signals from the apparatus comprising signal information, and
software in the processor performing an analytic procedure on the information to provide information regarding the specimen.

* * * * *